United States Patent [19]
Kararli et al.

[11] Patent Number: 5,935,939
[45] Date of Patent: Aug. 10, 1999

[54] STABILIZED DISPERSIONS OF MISOPROSTOL

[75] Inventors: Tugrul T. Kararli, Skokie; David Otto, Vernon Hills; Stanley C. Penzotti, Jr., Green Oaks; James E. Truelove, Libertyville, all of Ill.

[73] Assignee: G. D. Searle & Co., Chicago, Ill.

[21] Appl. No.: 08/709,708

[22] Filed: Sep. 9, 1996

Related U.S. Application Data

[63] Continuation of application No. 08/457,914, Jun. 1, 1995, abandoned.

[51] Int. Cl.$^6$ ............................................ A61K 31/70
[52] U.S. Cl. ........................ 514/54; 514/59; 514/60; 514/573; 514/937; 514/947; 514/970; 560/121; 562/503
[58] Field of Search ........................... 562/503; 560/121; 514/573, 947, 970, 54, 59, 60, 937

[56] References Cited

U.S. PATENT DOCUMENTS

| | | | |
|---|---|---|---|
| 4,058,623 | 11/1977 | Hoffmann et al. | 424/317 |
| 4,113,882 | 9/1978 | Okazaki et al. | 424/317 |
| 4,211,793 | 7/1980 | Lodhi et al. | 424/305 |
| 4,301,146 | 11/1981 | Sanvordeker | 424/80 |
| 4,335,097 | 6/1982 | David et al. | 424/14 |
| 4,352,790 | 10/1982 | Johansson et al. | 424/78 |
| 4,431,833 | 2/1984 | Lodhi et al. | 560/2 |
| 4,684,632 | 8/1987 | Schulz et al. | 514/78 |
| 5,120,719 | 6/1992 | Iwamoto et al. | 514/54 |

OTHER PUBLICATIONS

Yamamoto, et al., "Improvement of Stability and Dissolution of Prostaglandin $E_1$ by Maltosyl–β–cyclodextrin in Lyophilized Formulation". *Chem. Pharm. Bull.,* 40(3) 747–751(1992).

Yalkowsky, et al., "Stability of E–Type Prostaglandins in Triacetin". *J. Pharm. Sciences* vol.68, No. 1, pp. 114–115 (1979).

Harris, et al., "Pharmaceutical Aspects of Prostaglandin Formulations for Local Administration in Obstetrics". *Pharmacy International,* pp. 113–118 (1981).

Adachi, et al., "Stabilization of Prostaglandin $E_1$ in Fatty Alcohol Propylene Glycol Ointment by Acidic Cyclodextrin Derivative, O–Carboxymethyl–O–ethyl–β–cyclodextrin", *Chem. Pharm. Bull.,* 40(6) 1586–1591 (1992).

Inaba, et al., "Prostaglandins and Their Cyclodextrin Complexes". *J. Inclusion Phenomena,* 2, 467–474 (1984).

*Primary Examiner*—James O. Wilson
*Attorney, Agent, or Firm*—Cynthia S. Kovacevic

[57] ABSTRACT

The present invention provides for stabilization of misoprostol in solid dispersions using amorphous excipients or excipients which have been converted to an amorphous state such as hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polyethylene glycol, starch, polypropylene, dextrans, dextrins, hydroxypropyl β-cyclodextrin chitosan, co-(lactic/glycolic)copolymers, poly(orthoester), polyvinyl chloride, polyvinyl acetate, ethylene vinyl acetate, lectins, carbopols, silicon elastomers, cyclodextrins, polyacrylic polymers, maltodextrins, lactose, fructose, inositol, trehalose, maltose, and raffinose, (and other mono-, di- and tri- saccharides) and α-, β- and γ-cyclodextrins, and more preferably the excipients which are used are dextran, maltodextrin, hydroxypropyl β-cyclodextrin and maltose.

9 Claims, No Drawings

STABILIZED DISPERSIONS OF MISOPROSTOL

This is a FILE-WRAPPER CONTINUATION of application Ser. No. 08/457,912, filed Jun. 1, 1995 now abandoned.

FIELD OF INVENTION

The invention herein relates to amorphous solid state dispersions of misoprostol, methods of preparing the dispersions and the use of such dispersions in pharmaceutical formulations.

BACKGROUND OF INVENTION

Misoprostol is a compound of the formula

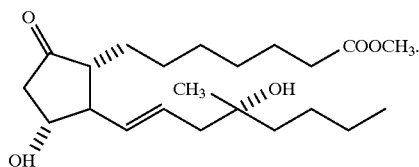

Misoprostol is classified in a group of compounds generally known as prostaglandins. Prostaglandins exhibit a variety of beneficial biological responses and therefore are useful as pharmaceutical agents. In particular misoprostol is a known inhibitor of gastric acid secretion and is also known to possess mucosal protective properties. Misoprostol, as a pharmaceutical agent, is therefore useful in preventing gastric ulcers.

Generally, prostaglandins are difficult to formulate into stable pharmaceutical dosage forms because of their relative instability. Prostaglandins tend to decompose above room temperature and in the presence of small amounts of acid, base or water. For example, at 55° C., 75% of the prostaglandin, misoprostol, degrades in 4 weeks. The problem to be addressed in developing prostaglandin formulations has been how to stabilize the prostaglandin without loss of pharmacological activity. Various attempts have been made at stabilizing prostaglandins for use in pharmaceutical dosage forms.

U.S. Pat. No. 4,301,146 discloses solid state dispersions of misoprostol, a prostaglandin derivative in hydroxypropyl methylcellulose (HPMC) and polyvinyl pyrrolidone (PVP) in combination with other tablet and capsule excipients.

Complexation with various cyclodextrins has been used to stabilize various prostaglandins. [See for example Inaka et al., *J. Inclusion Phenomena*, 2:467–474 (1984)]. U.S. Pat. No. 4,113,882 describes the use of lyophilized compositions containing, dextran, dextrin, thiol compounds, a lower alkylcellulose or deoxycholic acid salts for stabilization of PGE type compounds. JP 53050141 describes a tricaprylin solution as a relatively stable media for PGE2. DE 2515001 describes a freeze-dried powder, containing polyvinylpyrrolidone (PVP) as a stable media for $PGE_2$. JP 53148518 describes freeze-dried bentonite as a stable media for $PGE_2$. JP 53130417 describes freeze-dried starch as a stable media for $PGE_2$. JP 60169430 describes various preservatives and antioxidants in coconut oil as a stable media for a $PGE_1$ derivative. EP 260719 describes the use of polyvinylacetate in the stabilization of $PGE_2$. Yalkowski et al. [*J. Pharm. Sci.*, 68:114–115 (1979)] describe the use of triacetin in the stabilization of a $PGE_2$ derivative.

Due to the usefulness of prostaglandins as pharmacological agents and because of their instability in pharmaceutical dosage forms, there is a continuing need for stabilizing prostaglandins, including misoprostol, for use in pharmaceuticals. The present invention provides stabilized amorphous solid state dispersions of misoprostol, which formulations can be used in preparing pharmaceutical dosage forms.

SUMMARY OF THE INVENTION

The present invention provides stable dispersions of the prostgalandin misoprostol in solid state. The stable dispersions are amorphous dispersions which remain relatively stable over time at various temperatures. The present dispersions are therefore useful in preparing pharmaceutical compositions containing the active agent misoprostol. More particularly the present invention provides for stabilized misoprostol amorphous dispersions which are prepared using the following amorphous or semi-crystalline excipients, hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polypropylene, dextrans, dextrins, hydroxypropyl-β cyclodextrin, chitosan, co-(lactic/glycolic)copolymers, poly(orthoester), poly(anhydrate), polyvinyl chloride, polyvinyl acetate, ethylene vinyl acetate, lectins, carbopols, silicon elastomers, polyacrylic polymers, and maltodextrins or the following crystalline or semi-crystalline excipients which can be converted to an amorphous or semi-crystalline state lactose, fructose, inositol, trehalose, maltose, and raffinose and α-, β and γ-cyclodextrins.

The dispersions are generally prepared by three methods. In one method the misoprostol is solubilized in ethanol and the excipient dispersed in the solution, followed by evaporation of the solvent. In a second method water solutions of misoprostol and the excipient are lyophilized. The third method employs spray-drying of water solutions of misoprostol and the excipient.

DETAILED DESCRIPTION OF THE INVENTION

The dispersions of the present invention can be prepared by various techniques. In the solvent method, drug is dissolved in an organic solvent, such as ethanol, and the excipient is added and mixed with the drug solution. The solvent is then evaporated. In the lyophilization method, drug and excipient are dissolved in water, the solution is frozen then the ice is removed. In the spray drying technique, a solution of drug and excipient in water is spray dried to produce a powder dispersion.

The present invention provides for stabilization of misoprostol in solid dispersions using amorphous excipients or excipients which have been converted to an amorphous state such as hydroxypropyl cellulose, methyl cellulose, carboxymethyl cellulose, sodium carboxymethyl cellulose, cellulose acetate phthalate, cellulose acetate butyrate, hydroxyethyl cellulose, ethyl cellulose, polyvinyl alcohol, polyethylene glycol, starch, polypropylene, dextrans, dextrins, hydroxypropyl β-cyclodextrin chitosan, co-(lactic/glycolic)copolymers, poly(orthoester), polyvinyl chloride, polyvinyl acetate, ethylene vinyl acetate, lectins, carbopols, silicon elastomers, cyclodextrins, polyacrylic polymers, maltodextrins, lactose, fructose, inositol, trehalose, maltose, and raffinose, (and other mono-, di- and tri- saccharides) and α-, β- and β-cyclodextrins, and more preferably the excipients which are used are dextran, maltodextrin, hydroxypropyl β-cyclodextrin and maltose. All of the excipients used to prepare the dispersions of the present invention are commercially available or can be prepared by known methodology. Lactose, maltose and mannitol were supplied as crystalline powders. Maltose was converted to a stable amorphous solid after lyophilization or spray drying.

Dispersions of misoprostol were prepared using the ethanol solvent method, lyophilization and spray drying techniques. Generally, the ethanol solvent method involves: 1) dissolving the excipient in ethanol or another suitable solvent; 2) dissolving misoprostol in ethanol or another suitable solvent; 3) adding the misoprostol solution to the excipient solution; [or alternatively for 2) and 3) misoprostol oil can be added directly into the solvent containing the excipient]; 4) stirring the resulting solution; 5) evaporating the solvent to dryness using a flash evaporator; and 6) drying and sieving or grinding the resulting solid dispersion.

The lyophilization technique involves dissolving misoprostol and the excipient in water at room temperature. The solution is then freeze-dried using a commercially available lyophilizer in an ordinary manner and dried.

The spray drying technique involves dissolving misoprostol and the excipient in water at room temperature. The solutions are spray dried with a 115–150° C. inlet temperature and a 70–90° C. outlet temperature at a feed rate of 10 ml/min. to 30 ml/min. and a 12 1/min. atomization rate. Particles of 1–20 micrometer diameter were generated.

The stability of the dispersions was assessed at 30, 40 and 55° C. The water levels in the dispersions were measured by the Karl Fisher method since there is a direct correlation between water levels and misoprostol stability. Differential scanning calorimetric (DSC) and microscopic analysis of the dispersions were performed to confirm the crystalline and amorphous nature of the excipients and dispersions.

The dispersions can be processed, using suitable auxiliary agents or excipients, into a variety of preparations suitable for oral, nasal, intravenous, intramuscular, subcutaneous, intravaginal, buccal, ocular, transdermal, aerosol and topical pharmaceutical dosage forms for delivery of the active agent misoprostol. The dispersions can be used in production of tablets, capsules, and bead formulations for oral delivery using standard methodology. The dispersions can be used directly or in combination with lactose type dispersants in a dry powder delivery device for pulmonary delivery of misoprostol. Meter dose inhalers can be prepared using a suspension of these dispersions in the propellants used in aerosol formulations. The dispersions can be used in transmucosal (buccal) or intravaginal delivery forms of misoprostol. These formulations are prepared in combination with one or two polymers that provide a stable media for misoprostol. The dispersions can be used in the nasal delivery of misoprostol in powder form using dry powder delivery devices. Such misoprostol formulations may be used for treatment of allergic rhinitis. Nasal delivery is also effective for delivering misoprostol systemically.

The ratio of misoprostol to excipient can be varied over wide ranges and depends on the concentration of misoprostol required in the pharmaceutical dosage form ultimately administered.

However, the preferred range of excipient to misoprostol is 0.1–20% and more preferably is 1%. In the foregoing the percentages are by weight.

The following examples further illustrate specific embodiments of the present invention, and are considered illustrative, but not limiting, descriptions of the invention.

EXAMPLES OF DISPERSIONS PREPARED BY THE SOLVENT METHOD

Example 1

50 g polyvinyl pyrollidone (PVP) [Kollidon, (PF 12)] was dissolved in 170 ml ethanol in a round bottom flask. 0.5 g misoprostol was dissolved in 1–2 ml ethanol and then added into the ethanol/PVP solution. The ethanol content of the misoprostol/ethanol/PVP solution was evaporated in a rotary evaporator and the resultant cake was dried under high vacuum. The dispersion was first ground using a mortar and pestle and then milled in an air-jet mill. The dispersion was further dried in a high vacuum oven overnight at 25–35° C. to minimize the moisture and solvent content. The stability of the dispersion was assessed at 30, 40 and 55° C. The results are summarized in Table 1A, 1B and 1C along with the moisture content. The DSC and microscopic examination of the dispersion did not indicate any crystallinity.

Example 2

50 g maltodextrin (Maltrin M040) was added into 250 ml ethanol while stirring the ethanol in a round bottom flask. 0.5 g misoprostol was dissolved in 1–2 ml ethanol and then added into the ethanol/maltodextrin suspension. The ethanol content of the misoprostol/ethanol/ maltodextrin suspension was evaporated using a rotary evaporator and the resultant powder was dried under high vacuum overnight. The powder dispersion was milled in an air-jet mill and dried further in a high vacuum oven overnight at 25–35° C. to minimize the moisture and solvent content. The stability of the dispersion at 30, 40 and 55° C. is summarized in Table 2A, 2B and 2C along with the moisture content. The DSC and microscopic examination of the dispersion did not indicate any crystallinity.

Example 3

50 g dextran (MW 10,000) was added into 250 ml ethanol while stirring the ethanol in a round bottom flask. 0.5 g misoprostol was dissolved in 1–2 ml ethanol and then added into the ethanol/dextran suspension. The ethanol content of the misoprostol/ethanol/dextran suspension was evaporated using a rotary evaporator. The resultant powder was dried under high vacuum overnight. The powder dispersion was milled in an air-jet mill and dried further in a high vacuum oven overnight at 25–35° C. to minimize the moisture and solvent content. The stability of the dispersion was determined at 30, 40 and 55° C. The results are summarized in Table 3A, 3B and 3C along with the moisture content. The DSC and microscopic examination of the dispersion did not indicate any crystallinity.

Example 4

50 g lactose monohydrate, NF, spray dried was added into 250 ml ethanol while stirring the ethanol in a round bottom flask. 0.5 g misprostol was dissolved in 1–2 ml ethanol and then added into the ethanol/lactose suspension. The ethanol content of the misoprostol/ ethanol/lactose suspension was evaporated using a rotary evaporator. The resultant powder product was dried under high vacuum overnight. The powder dispersion was milled in an air-jet mill and further dried in a high vacuum oven overnight at 25–35° C. to minimize the moisture and ethanol content. The stability of the dispersion was determined at 30, 40 and 55° C. The results are tabulated in Table 4A along with the moisture content. The DSC and microscopic examination of the dispersion indicated mainly crystalline structure.

Example 5

50 g maltose was added into 250 ml ethanol while stirring the ethanol in a round bottom flask. 0.5 g misoprostol was then added into the ethanol/maltose suspension. The ethanol content of the misoprostol/ethanol/maltose suspension was evaporated using a rotary evaporator. The resultant powder product was dried under high vacuum overnight. The powder dispersion was further dried in a high vacuum oven overnight at 40° C. to minimize the moisture and ethanol content. The stability of the dispersion was determined at 55° C. The results are tabulated in Table 5. The DSC and microscopic examination of the dispersion indicated mainly crystalline structure.

EXAMPLES OF LYOPHILIZED DISPERSIONS

Example 6

In a 3 L round bottom flask, 0.38 g misoprostol oil was dissolved in 1.2 L water. In 375 ml of this solution, 10 g dextran was dissolved. The resulting solution was quickly frozen around the surface of the flask by spinning the flask in dry ice/acetone. The frozen cake was lyophilized at room temperature using a Virtis Freeze Mobile 12 lyophilizer. The dispersion was dried in a high vacuum oven at room temperature overnight. The stability of the dispersion was determined at 55° C. The results are summarized in Table 6 along with the moisture content. The DSC and microscopic examination of the dispersion did not indicate any crystallinity.

Example 7

10 g of maltodextrin (Maltrin, M040) was dissolved in 375 ml of the misoprostol/water solution from Example 6. The resulting solution was quickly frozen around the surface of the flask by spinning the flask in dry ice/acetone. The contents of the flask was lyophilized at room temperature using a Virtis Freeze Mobile 6 lyophilizer. The dispersion was dried in a high vacuum oven at room temperature overnight. The stability of the dispersion was determined at 55° C. The results are summarized in Table 7 along with the moisture content. The DSC and microscopic examination of the dispersion did not indicate any crystallinity.

Example 8

In 375 ml of the misoprostol/water solution from Example 6, 10 g PVP (Kollidon 12 PF) was dissolved. The resulting solution was quickly frozen around the surface of the flask by spinning the flask in dry ice/acetone. The frozen cake was lyophilized at room temperature using a Virtis Freeze Mobile 12 lyophilizer. The dispersion was dried in a high vacuum oven at room temperature overnight. The stability of the dispersion was determined at 55° C. The results are summarized in Table 8 along with the moisture content. The DSC and microscopic examination of the dispersion did not indicate any crystallinity.

Example 9

In a 5 L round bottom flask, 0.25 g misoprostol oil and 25 g maltose were dissolved in 800 ml water. The resulting solution was transferred into two 5 L flasks and quickly frozen as cake around the surface of the flask by swirling in dry ice/acetone. The frozen cake was lyophilized at room temperature to dryness using a Virtis Freeze Mobile 12 lyophilizer. The dispersion was dried in a high vacuum oven at room temperature overnight. The stability of the dispersion was determined at 55° C. The results are summarized in Table 9 along with the moisture content data. The DSC and microscopic examination of the dispersion did not indicate any crystallinity.

Example 10

In a 5 L round bottom flask, 0.25 g misoprostol oil and 25 g mannitol was dissolved in 800 ml water. The resulting solution was quickly frozen as cake around the surface of the flask by swirling the flask in dry ice/acetone. The cake was lyophilized at room temperature to dryness using a Virtis Freeze Mobile 12 lyophilizer. The dispersion was dried overnight in a high vacuum oven at room temperature. The stability of the dispersion was determined at 55° C. The results are summarized in Table 10 along with the moisture content data. The DSC and microscopic examination of the dispersion indicated mainly crystalline structure.

Example 11

In a 5 L round bottom flask, 0.28 g misoprostol oil and 25 g lactose, monohydarate NF, spray dried were dissolved in 775 ml water. The resulting solution was transferred into two 5 L flasks and quickly frozen as cake around the surface of the flasks by swirling the flasks in dry ice/acetone. The cake was lyophilized at room temperature using a Virtis Freeze Mobile 12 lyophilizer. The dispersion was dried overnight in a high vacuum oven at room temperature. The analysis of the dispersion right after the processing indicated only 58% misoprostol remained. The DSC and microscopic examination of the dispersion indicated a mainly crystalline nature.

Example 12

In a flask, 0.215 g misoprostol oil, 10.65 g maltodextrin (Maltrin, M040) and 10.65 g maltose were dissolved in 692 ml water. The resulting solution was quickly frozen as cake around the surface of a 5 L round bottom flask by swirling the flask in dry ice/acetone. The cake was lyophilized at room temperature using a Virtis 25 SL lyophilizer. The dispersion was dried overnight in a high vacuum oven at room temperature. The stability of the dispersion was determined at 55° C. The results are summarized in Table 11 along with the moisture content data. The DSC examination of the dispersion did not indicate any crystallinity.

Example 13

In a flask, 0.20 g misoprostol oil, 5.0 g maltodextrin (Maltrin, M040) and 15.0 maltose were dissolved in 700 ml water. The resulting solution was quickly frozen as a cake around the surface of a 5 L round bottom flask by swirling the flask in dry ice/acetone. The cake was lyophilized at room temperature using a Virtis 25 SL lyophilizer. The dispersion was dried overnight in a high vacuum oven at 40° C. The stability of the dispersion was determined at 30 and 55° C. The results are summarized in Table 12 along with the moisture content data. The DSC examination of the dispersion did not indicate any crystallinity.

Example 14

In a flask 0.16 g misoprostol oil and 15 g hydroxypropyl-β-cyclodextrin were dissolved in 480 ml water. The resulting solution was quickly frozen as a cake around the surface of a 5 L round bottom flask by swirling the flask in dry ice/acetone. The cake was lyophilized at room temperature using a Virtis 25 SL lyophilizer. The dispersion was dried overnight in a high vacuum oven at 40° C. The stability of the dispersion was determined at 55° C. The results are summarized in Table 13 along with moisture content data. The DSC examination of the dispersion did not indicate any crystallinity.

EXAMPLES OF SPRAY DRIED DISPERSIONS

Example 15

In a flask, 0.23 g misoprostol and 23 g PVP were dissolved in 937 ml distilled water. This solution was spray dried using a Niro Atomizer Mobile Minor spray drier. The atomizer pressure was 2.8–3.9 bars and feed rate was 15–30 ml/min. The inlet and outlet temperatures were 119–140° C. and 74–85° C., respectively. The dispersions were dried overnight in a high vacuum oven at 40° C. The stability of the dispersion was determined at 55° C. The results are summarized in Table 14 along with the moisture content data. The differential scanning calorimetric (DSC) and microscopic examination of the dispersion did not indicate any crystallinity.

Example 16

In a 2 L flask, 0.25 g misoprostol and 25 g maltose were dissolved in 1000 ml distilled water. This solution was spray dried using a Niro Atomizer Mobile Minor spray drier. The atomizer pressure was 2.8–3.9 bars and feed rate was 15–20 ml/min. The inlet and outlet temperatures were 140° C. and 85° C., respectively. The dispersions were dried overnight in a high vacuum oven at 40° C. The stability of the dispersion was determined at 55° C. The results are summarized in Table 14 along with the moisture content data. The DSC and microscopic examination of the dispersion did not indicate any crystallinity.

Example 17

In a 2 L flask, 0.30 g misoprostol and 30 g maltodextrin (Maltrin, M040) were dissolved in 1200 ml distilled water. The solution was spray dried using a Niro Atomizer Mobile Minor spray drier. The atomizer pressure and feed rate were 4.4 bars and 10–20 ml/min, respectively. The inlet and outlet temperatures were 119–142° C. and 75–89° C., respectively. The dispersions were dried overnight in a high vacuum oven at 40° C. The stability of the dispersion was determined at 55° C. The results are summarized in Table 14 along with the moisture content data. The differential scanning calorimetric (DSC) and microscopic examination of the dispersion did not indicate any crystallinity.

Example 18

In a flask, 0.28 g misoprostol and 28 g dextran were dissolved in 1140 ml distilled water. The solution was spray dried using a Niro Atomizer Mobile Minor spray drier. The atomizer pressure was 2.8–3.9 bars and feed rate was 15–20 ml/min. The inlet and outlet temperatures were 140° C. and 85° C., respectively. The dispersions were dried overnight in a high vacuum oven at 40° C. The stability of the dispersion was determined at 55° C. The results are summarized in Table 14 along with the moisture content data. The DSC and microscopic examination of the dispersion did not indicate any crystallinity.

TABLE 1A

EXAMPLE 1 - MISOPROSTOL/PVP (55° C.)

| | TIME (WEEKS) | | | | | | |
|---|---|---|---|---|---|---|---|
| 0 | 1 | 2 | 3 | 4 | 6 | 8 | 12 |
| % MISOPROSTOL REMAINING 94.3 ± 0.6 | 91.7 ± 0.1 | 90.1 ± 0.3 | 88.0 ± 0.6 | 87.0 ± 0.4 | 83.7 ± 1.4 | 80.4 ± 0.9 | 78.0 ± 1.6 |

MOISTURE: (%)
0 WEEK 1.2
8 WEEK 2.7 ± 0.6

TABLE 1B

EXAMPLE 1 - MISOPROSTOL/PVP (40° C.)

| | TIME (WEEKS) | | | |
|---|---|---|---|---|
| 0 | 2 | 4 | 8 | 14 |
| % MISOPROSTOL REMAINING 94.3 ± 0.6 | 96.8 ± 3.6 | 92.9 ± 0.5 | 93.0 ± 0.4 | 90.7 ± 0.5 |

TABLE 1C

EXAMPLE 1 - MISOPROSTOL/PVP (30° C.)

| | TIME (WEEKS) | | |
|---|---|---|---|
| 0 | 6 | 12 | 18 |
| % MISOPROSTOL REMAINING 94.3 ± 0.6 | 94.4 ± 1.2 | 92.7 ± 1.2 | 94.0 ± 4.7 |

TABLE 2A

EXAMPLE 2 - MISOPROSTOL/MALTODEXTRIN (55° C.)

| | TIME (WEEKS) | | | | | | |
|---|---|---|---|---|---|---|---|
| | 0 | 1 | 3 | 4 | 6 | 8 | 12 |
| % MISOPROSTOL REMAINING | 96.6 ± 3.0 | 96.2 ± 7.8 | 92.2 ± 2.1 | 92.1 ± 0.4 | 84.0 ± 1.1 | 79.5 ± 3.3 | 66.0 ± 2.7 |

MOISTURE: (%)
0 WEEK 3.2 ± 0.8
8 WEEK 3.5 ± 0.9

TABLE 2B

EXAMPLE 2 - MISOPROSTOL:MALTODEXTRIN (40° C.)

| | TIME (WEEKS) | | | |
|---|---|---|---|---|
| | 0 | 4 | 8 | 14 |
| % MISOPROSTOL REMAINING | 96.6 ± 3.0 | 95.3 ± 0.7 | 93.7 ± 0.3 | 93.9 ± 2.2 |

TABLE 2C

EXAMPLE 2 - MISOPROSTOL:MALTODEXTRIN (30° C.)

| | TIME (WEEKS) | | | |
|---|---|---|---|---|
| | 0 | 6 | 12 | 18 |
| % MISOPROSTOL REMAINING | 96.6 ± 3.0 | 97.0 ± 1.9 | 98.9 ± 3.1 | 98.1 ± 2.0 |

TABLE 3A

EXAMPLE 3 - MISOPROSTOL:DEXTRAN (55° C.)

| | TIME (WEEKS) | | | | | | |
|---|---|---|---|---|---|---|---|
| | 0 | 1 | 3 | 4 | 6 | 8 | 12 |
| % MISOPROSTOL REMAINING | 92.6 ± 2.8 | 92.1 ± 4.0 | 86.7 ± 3.1 | 85.6 ± 3.1 | 81.3 ± 4.2 | 72.1 ± 1.0 | 61.4 ± 2.1 |

MOISTURE: (%)
0 WEEK 3.1 ± 0.3
8 WEEK 3.4 ± 0.8

TABLE 3B

EXAMPLE 3 - MISOPROSTOL:DEXTRAN (40° C.)

| | TIME (WEEKS) | | | |
|---|---|---|---|---|
| | 0 | 4 | 8 | 14 |
| % MISOPROSTOL REMAINING | 92.6 ± 2.8 | 93.4 ± 1.7 | 90.2 ± 1.9 | 80.2 ± 4.1 |

TABLE 3C

EXAMPLE 3 - MISOPROSTOL:DEXTRAN (30° C.)

| | TIME (WEEKS) | | | |
|---|---|---|---|---|
| | 0 | 6 | 12 | 18 |
| % MISOPROSTOL REMAINING | 92.6 ± 2.8 | 90.2 ± 2.1 | 84.0 ± 1.1 | 88.5 ± 1.6 |

TABLE 4A

EXAMPLE 4 - MISOPROSTOL:LACTOSE (55° C.)

| | TIME (WEEKS) | | | | |
|---|---|---|---|---|---|
| | 0 | 1 | 3 | 4 | 6 |
| % MISOPROSTOL REMAINING | 102.1 ± 6.5 | 4.1 ± 0.1 | 2.7 ± 0.3 | 3.8 ± 0.6 | 2.5 ± 0.1 |

MOISTURE: (%)
0 WEEK 4.8 ± 0.1
8 WEEK 4.9 ± 0.0

TABLE 5

EXAMPLE 5 - MISOPROSTOL:MALTOSE DISPERSION (55° C.)

| | TIME (WEEKS) | |
|---|---|---|
| | 0 | 3 |
| % MISOPROSTOL REMAINING | 86.4 ± 5.6 | 28.7 ± 7.9 |

MOISTURE: (%)
0 WEEK 4.9 ± 0.1
3 WEEK 5.0 ± 0.2

TABLE 6

EXAMPLE 6 - MISOPROSTOL:DEXTRAN (55° C.)

| | TIME (WEEKS) | | |
|---|---|---|---|
| | 0 | 6 | 9 |
| % MISOPROSTOL REMAINING | 92.4 ± 0.7 | 82.4 | 73.9 |

MOISTURE (%) 5.0 ± 0.5

TABLE 7

EXAMPLE 7 - MISOPROSTOL:MALTODEXTRIN (55° C.)

| | TIME (WEEKS) | | |
|---|---|---|---|
| | 0 | 6 | 9 |
| % MISOPROSTOL REMAINING | 100.2 ± 0.7 | 73.9 | 80.7 |

MOISTURE (%) 5.2 ± 0.6

TABLE 8

EXAMPLE 8 - MISOPROSTOL:PVP (55° C.)

| | TIME (WEEKS) | | |
|---|---|---|---|
| | 0 | 6 | 9 |
| % MISOPROSTOL REMAINING | 89.9 ± 0.8 | 78.2 | 72.2 |

MOISTURE (%) 2.0 ± 0.3

TABLE 9

EXAMPLE 9 - MISOPROSTOL:MALTOSE (55° C.)

| | TIME (WEEKS) | | | |
|---|---|---|---|---|
| | 0 | 2 | 6 | 9 |
| % MISOPROSTOL REMAINING | 97.0 ± 1.4 | 95.6 ± 1.5 | 85.1 | 78.4 |

MOISTURE (%) 4.4 ± 0.0

TABLE 10

EXAMPLE 10 - MISOPROSTOL:MANNITOL (55° C.)

| | TIME (WEEKS) |
|---|---|
| | 0 |
| % MISOPROSTOL REMAINING | 8.5 ± 1.7 |

TABLE 11

EXAMPLE 12 - MISOPROSTOL:MALTOSE:MALTODEXTRIN (50:50) (55° C.)

| | TIME (WEEKS) | |
|---|---|---|
| | 0 | 8 |
| % MISOPROSTOL REMAINING | 96.2 ± 1.8 | 80.5 ± 1.4 |

MOISTURE (%) 0.6 ± 0.1

TABLE 12

EXAMPLE 13 - MISOPROSTOL:MALTOSE:MALTODEXTRIN (75:25) (55° C.)

| | TIME (WEEKS) | |
|---|---|---|
| | 0 | 12 |
| % MISOPROSTOL REMAINING | 88.3 ± 2.6 | 78.6 ± 3.9 |

MOISTURE (%) 3.3 ± 0.9

TABLE 13

EXAMPLE 14 - MISOPROSTOL:HYDROXYPROPYL β-CYCLODEXTRIN (55° C.)

| | TIME (WEEKS) | | |
|---|---|---|---|
| | 0 | 3 | 12 |
| % MISOPROSTOL REMAINING | 102.7 ± 1.9 | 95.8 ± 1.7 | 76.9 ± 4.6 |

MOISTURE (%) 3.7 ± 0.2
3.8 ± 0.0

TABLE 14

EXAMPLE 15 - MISOPROSTOL:PVP (55° C.)

| | TIME (WEEKS) | |
|---|---|---|
| | 0 | 8 |
| % MISOPROSTOL REMAINING | 82.1 ± 0.6 | 75.8 ± 0.8 |

MOISTURE (%) 3.0 ± 0.1

| EXAMPLE 16 - MISOPROSTOL:MALTOSE (55° C.) | | |
|---|---|---|
| | TIME (WEEKS) | |
| | 0 | 8 |
| % MISOPROSTOL REMAINING | 81.6 ± 0.2 | 65.9 ± 1.3 |

MOISTURE (%) 2.1 ± 0.1

| EXAMPLE 17 - MISOPROSTOL:MALTODEXTRIN (55° C.) | | |
|---|---|---|
| | TIME (WEEKS) | |
| | 0 | 8 |
| % MISOPROSTOL REMAINING | 85.9 ± 0.9 | 79.3 ± 3.7 |

MOISTURE (%) 3.6 ± 0.6

| EXAMPLE 18 - MISOPROSTOL:DEXTRAN (55° C.) | | |
|---|---|---|
| | TIME (WEEKS) | |
| | 0 | 8 |
| % MISOPROSTOL REMAINING | 88.9 ± 0.4 | 78.1 ± 1 |

MOISTURE (%) 1.7 ± 0.5

The data presented in the tables show that the amorphous dispersions provide stability for misoprostol whereas those dispersions which were crystalline did not provide stability for misoprostol. For example, lactose and maltose which are enomers, were both used to prepare dispersions containing misoprostol. However, only maltose was prepared as an amorphous solid through lyophilization or spray drying under the conditions of the experiments. In amorphous maltose, misoprostol was stable (Examples 9 and 16). Misoprostol degraded relatively rapidly in maltose dispersions prepared using the ethanol solvent method which were not amorphous but crystalline (Example 5). Misoprostol degraded very rapidly in dispersion with lactose which was not in an amorphous state (Examples 4 and 11). The mannitol dispersion which was also crystalline was an unstable media for misoprostol (Example 10). These results suggest that the amorphous nature of the excipient is a prerequisite for the preparation of stable misoprostol dispersions. Thus if an excipient is amorphous or can be made amorphous it will provide stability for misoprostol in dispersion if no chemical incompatibility exists between misoprostol and excipient.

We claim:

1. A stable solid state amorphous dispersion of misoprostol comprising misoprostol and an excipient selected from (a) an excipient in an amorphous state selected from the group consisting of hydroxypropyl cellulose, methyl cellulose, carboxymethyl cellulose, cellulose acetate phthalate, cellulose acetate butyrate, hydroxyethyl cellulose, ethyl cellulose, polyvinyl alcohol, polyethylene glycol, polypropylene, dextrans, starch, dextrins, hydroxypropyl-β-cyclodextrin, chitosan, co-(lactic/glycolic)-copolymers, poly(orthoester), poly(anhydrate), polyvinyl chloride, polyvinylacetate, ethylene vinyl acetate, lectins, carbopols, silicon elastomers, polyacrylic polymers and maltodextrin; or (b) an amorphous or semi-crystalline excipient selected from the group consisting of monosaccharides, disaccharides and trisaccharides.

2. A stable solid state amorphous dispersion of misoprostol comprising misoprostol and an excipient in an amorphous state selected from the group consisting of dextran, hydroxypropyl β-cyclodextrin and maltodextrin.

3. A stable solid state amorphous dispersion of misoprostol comprising misoprostol and an excipient in an amorphous state or semi-crystalline form selected from the group consisting of monosaccharides, disaccharides and trisaccharides.

4. A stable solid state amorphous dispersion of misoprostol comprising misoprostol and an amorphous or semi-crystalline form of an excipient selected from the group consisting of fructose, lactose, inositol, maltose, trehalose and raffinose.

5. A dispersion according to claim 4 wherein the excipient is maltose.

6. A pharmaceutical composition comprising the stable solid state amorphous dispersion according to claim 1 wherein the misoprostol is present in a therapeutically effective amount and a pharmaceutically acceptable carrier.

7. A pharmaceutical composition comprising a solid state amorphous dispersion of misoprostol and an excipient in an amorphous state wherein the excipient is selected from the group consisting of dextran, hydroxypropyl β-cyclodextrin and maltodextrin.

8. A pharmaceutical composition comprising the stable solid state amorphous dispersion according to claim 3 wherein the misoprostol is present in a therapeutically effective amount and a pharmaceutically acceptable carrier.

9. A pharmaceutical composition according to claim 8 wherein the excipient is maltose.

* * * * *